(12) United States Patent
Batchelor et al.

(10) Patent No.: US 11,759,249 B2
(45) Date of Patent: Sep. 19, 2023

(54) DISENGAGEMENT MECHANISM FOR ELECTROSURGICAL FORCEPS

(71) Applicant: GYRUS ACMI, INC., Southborough, MA (US)

(72) Inventors: Kester J. Batchelor, Mound, MN (US); Theodore C. Blus, Shoreview, MN (US); Richard J. Curtis, Maple Grove, MN (US); Ryan J. Windgassen, Nowthen, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 768 days.

(21) Appl. No.: 16/085,745

(22) PCT Filed: Feb. 14, 2017

(86) PCT No.: PCT/US2017/017822
§ 371 (c)(1),
(2) Date: Sep. 17, 2018

(87) PCT Pub. No.: WO2017/172082
PCT Pub. Date: Oct. 5, 2017

(65) Prior Publication Data
US 2019/0046259 A1    Feb. 14, 2019

Related U.S. Application Data

(60) Provisional application No. 62/316,058, filed on Mar. 31, 2016.

(51) Int. Cl.
*A61B 18/00* (2006.01)
*A61B 18/12* (2006.01)
*A61B 18/14* (2006.01)

(52) U.S. Cl.
CPC ...... *A61B 18/1442* (2013.01); *A61B 18/1233* (2013.01); *A61B 2018/0091* (2013.01);
(Continued)

(58) Field of Classification Search
CPC ...... A61B 18/1442; A61B 2018/00922; A61B 2018/0091; A61B 2018/1462; A61B 18/1445; A61B 18/1447; A61B 18/1462
See application file for complete search history.

(56) References Cited

U.S. PATENT DOCUMENTS

| 4,041,952 A | 8/1977 | Morrison, Jr. et al. |
| 4,181,826 A | 1/1980 | Latasiewicz |

(Continued)

FOREIGN PATENT DOCUMENTS

| CN | 101511287 A | 8/2009 |
| CN | 105055020 A | 11/2015 |

(Continued)

OTHER PUBLICATIONS

International Search Report and Written Opinion for Application No. PCT/US2017/017822 dated Jul. 6, 2017.
(Continued)

*Primary Examiner* — Daniel W Fowler
*Assistant Examiner* — Annie L Shoulders
(74) *Attorney, Agent, or Firm* — Schwegman Lundberg & Woessner, P.A.

(57) ABSTRACT

An electrosurgical forceps comprising: (a.) a pair of working arms comprising; (i.) a first working arm and a second working arm, each of the first working arm and the second working arm having an inner surface; (ii.) one or more electrodes located on the inner surface of the first working arm, the second working arm, or both; and (b.) a selectively engageable activation system comprising; (i.) a control unit; (ii.) an activation switch; and (iii.) a disengagement mecha-
(Continued)

nism; wherein the first working arm and the second working arm are laterally movable relative to each other so that the activation switch is actuated when the disengagement mechanism is in an engaged position by closing the first working arm and the second working arm together, sending a signal to the control unit, which in turn sends a therapy signal to the one or more electrodes; wherein when the disengagement mechanism is in a disengagement position and the working arms are closed, the therapy signal is prevented from being sent from the control unit to the one or more electrodes.

19 Claims, 7 Drawing Sheets

(52) U.S. Cl.
CPC .............. *A61B 2018/00922* (2013.01); *A61B 2018/00946* (2013.01); *A61B 2018/00952* (2013.01); *A61B 2018/126* (2013.01); *A61B 2018/1412* (2013.01); *A61B 2018/1455* (2013.01); *A61B 2018/1462* (2013.01)

(56) References Cited

U.S. PATENT DOCUMENTS

| | | | |
|---|---|---|---|
| 4,256,931 A | 3/1981 | Palisek | |
| 4,319,099 A | 3/1982 | Asher | |
| 4,504,707 A | 3/1985 | Ochiai | |
| 4,703,139 A | 10/1987 | Dunlap | |
| 4,802,476 A | 2/1989 | Noerenberg et al. | |
| 4,846,516 A | 7/1989 | Yuh et al. | |
| 5,035,695 A | 7/1991 | Weber, Jr. et al. | |
| 5,071,426 A | 12/1991 | Dolgin et al. | |
| 5,226,904 A | 7/1993 | Gentelia et al. | |
| 5,376,765 A | 12/1994 | Holmes et al. | |
| 5,399,823 A | 3/1995 | McCusker | |
| 5,472,442 A | 12/1995 | Klicek | |
| 5,743,384 A | 4/1998 | Clark | |
| 6,110,171 A | 8/2000 | Rydell | |
| 6,113,596 A | 9/2000 | Hooven et al. | |
| 6,117,158 A * | 9/2000 | Measamer | A61B 17/2909 606/208 |
| 6,190,386 B1 | 2/2001 | Rydell | |
| 6,310,308 B1 | 10/2001 | Watson et al. | |
| 6,358,268 B1 | 3/2002 | Hunt et al. | |
| 6,423,918 B1 | 7/2002 | King et al. | |
| 6,551,313 B1 | 4/2003 | Levin | |
| 6,679,882 B1 | 1/2004 | Kornerup | |
| 7,179,258 B2 | 2/2007 | Buysse et al. | |
| 7,232,440 B2 | 6/2007 | Dumbauld et al. | |
| 7,687,734 B2 | 3/2010 | Weber | |
| 7,902,474 B2 | 3/2011 | Mittleman et al. | |
| 8,089,017 B2 | 1/2012 | Chen et al. | |
| 8,262,655 B2 | 9/2012 | Ghabrial et al. | |
| 8,378,240 B2 | 2/2013 | Rajagopal et al. | |
| 9,707,028 B2 | 7/2017 | Batchelor et al. | |
| 9,748,057 B2 | 8/2017 | Blus et al. | |
| 2004/0254573 A1 | 12/2004 | Dycus et al. | |
| 2005/0113827 A1 | 5/2005 | Dumbauld et al. | |
| 2005/0130697 A1 | 6/2005 | Dyer | |
| 2005/0154387 A1 | 7/2005 | Moses et al. | |
| 2005/0187512 A1 | 8/2005 | Isola et al. | |
| 2006/0084973 A1 | 4/2006 | Hushka | |
| 2007/0106297 A1 | 5/2007 | Dumbauld et al. | |
| 2007/0112343 A1 * | 5/2007 | Mische | A61B 18/20 606/41 |
| 2009/0171354 A1 * | 7/2009 | Deville | A61B 18/1445 606/51 |
| 2011/0077648 A1 | 3/2011 | Lee et al. | |
| 2011/0220479 A1 | 9/2011 | Zhou | |
| 2011/0288369 A1 | 11/2011 | Ginnebaugh et al. | |
| 2012/0059372 A1 * | 3/2012 | Johnson | A61B 18/1445 606/45 |
| 2012/0123405 A1 | 5/2012 | Moua et al. | |
| 2013/0178852 A1 * | 7/2013 | Allen, IV | A61B 18/12 606/42 |
| 2014/0005654 A1 * | 1/2014 | Batross | A61B 34/30 606/33 |
| 2014/0048397 A1 | 2/2014 | Sykes et al. | |
| 2014/0276795 A1 | 9/2014 | Batchelor et al. | |
| 2014/0276797 A1 * | 9/2014 | Batchelor | A61B 18/1233 606/42 |
| 2014/0276799 A1 | 9/2014 | Batchelor et al. | |
| 2015/0119885 A1 | 4/2015 | Windgassen et al. | |
| 2016/0058499 A1 | 3/2016 | Brooke | |
| 2016/0135872 A1 * | 5/2016 | Minnelli | A61B 17/320016 606/34 |
| 2017/0323744 A1 | 11/2017 | Blus et al. | |

FOREIGN PATENT DOCUMENTS

| | | |
|---|---|---|
| CN | 105380711 A | 3/2016 |
| CN | 105407823 A | 3/2016 |
| CN | 108430367 A | 8/2018 |
| CN | 109069200 A | 12/2018 |
| CN | 109069200 B | 6/2021 |
| EP | 1852078 A1 | 11/2007 |
| EP | 1852078 A1 | 11/2007 |
| EP | 1897506 A1 | 3/2008 |
| EP | 3435902 A1 | 2/2019 |
| JP | 2005144192 A2 | 6/2005 |
| JP | 2006102514 A | 4/2006 |
| JP | 2011072788 A | 4/2011 |
| JP | 2012075906 A | 4/2012 |
| JP | 2019513063 A | 5/2019 |
| JP | 6574069 B2 | 8/2019 |
| WO | WO-2014150682 A1 | 9/2014 |
| WO | WO-2016028882 A1 | 2/2016 |
| WO | WO-2017172082 A1 | 10/2017 |

OTHER PUBLICATIONS

Potentially Related U.S. Appl. No. 15/657,904, filed Jul. 24, 2017 published as US2017/0323744.
International Preliminary Report on Patentability for Application No. PCT/US2017/017822 dated Oct. 2, 2018.
Potentially Related U.S. Appl. No. 14/830,255, filed Aug. 19, 2018; published as US2016/0051314 on Feb. 25, 2016; granted as U.S. Pat. No. 9,707,028; Issued Jul. 18, 2017.
Potentially Related U.S. Appl. No. 15/801,379, filed Nov. 2, 2017.
Potentially Related U.S. Appl. No. 15/801,583, filed Nov. 2, 2017.
Potentially Related U.S. Appl. No. 15/801,533, filed Nov. 2, 2017.
Potentially Related U.S. Appl. No. 15/921,351, filed Mar. 14, 2018.
"Chinese Application Serial No. 201780020715.5, Office Action dated Aug. 17, 2020", w/ English translation, 20 pgs.
"Chinese Application Serial No. 201780020715.5, Response filed Office Action dated Aug. 17, 2020", w/English Claims, 14 pgs.
"European Application Serial No. 17708042.1, Communication Pursuant to Article 94(3) EPC dated Sep. 23, 2020", 6 pgs.
"European Application Serial No. 17708042.1, Response filed Jan. 25, 2021 to Communication Pursuant to Article 94(3) EPC dated Sep. 23, 2020", 4 pgs.

* cited by examiner

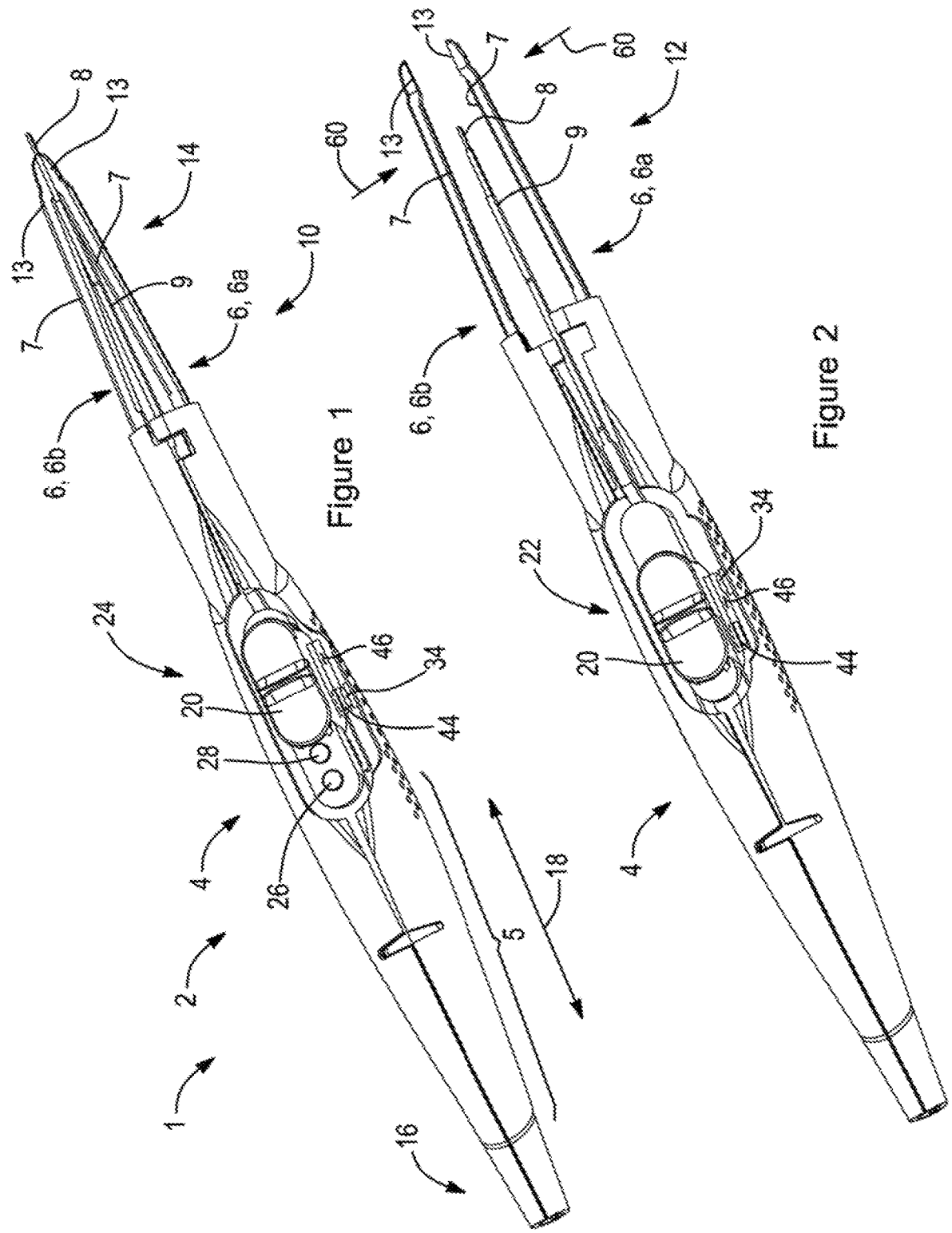

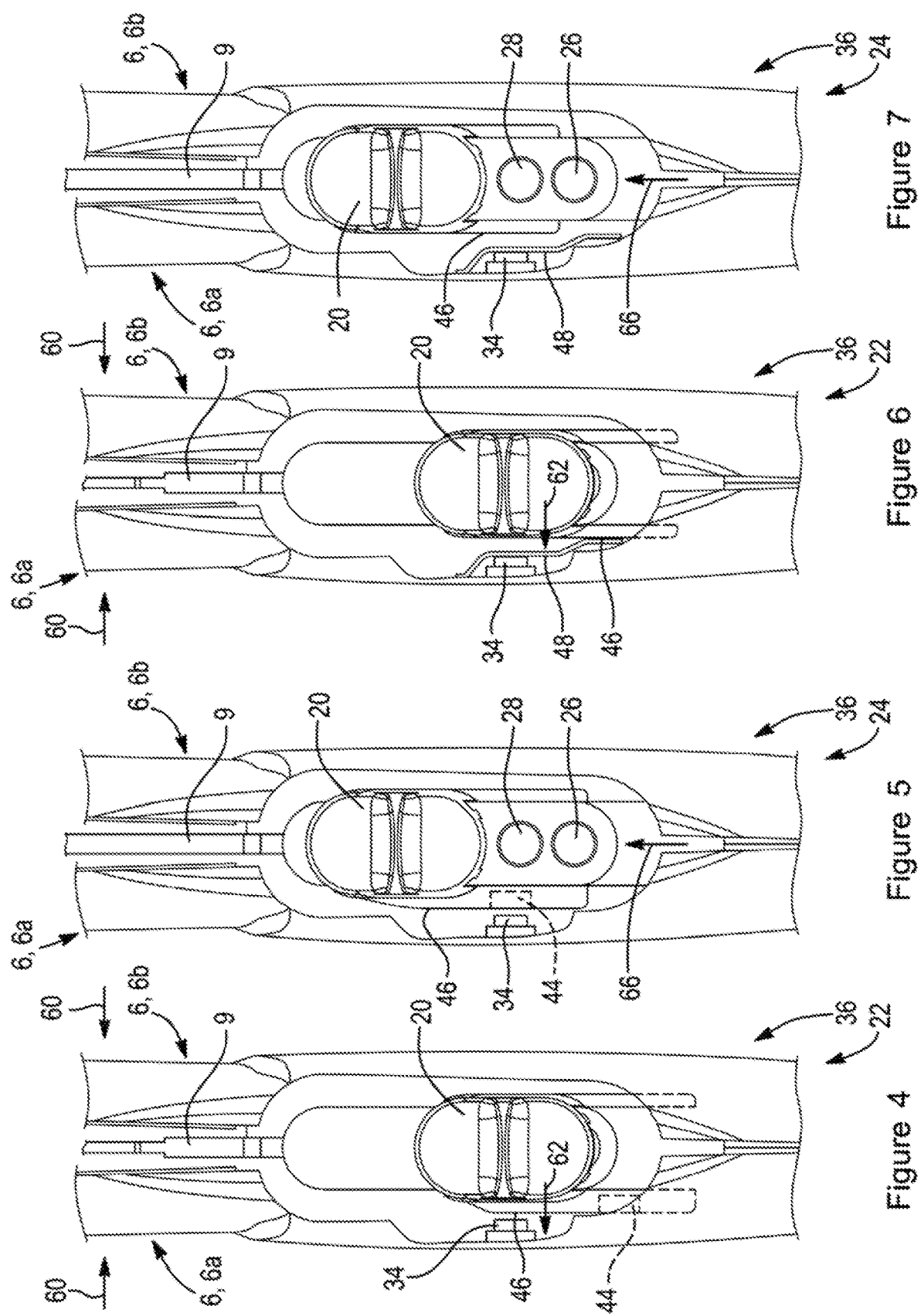

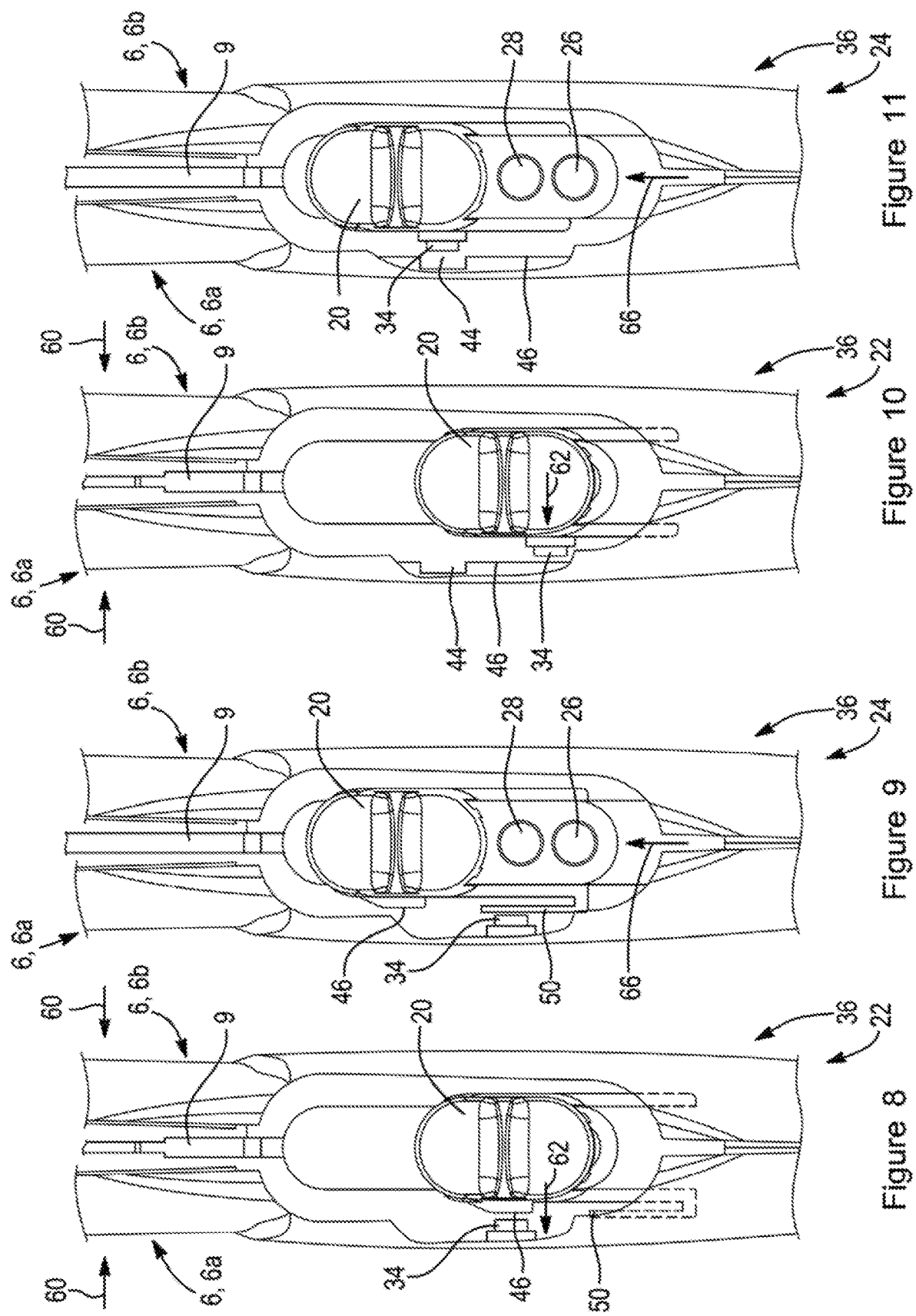

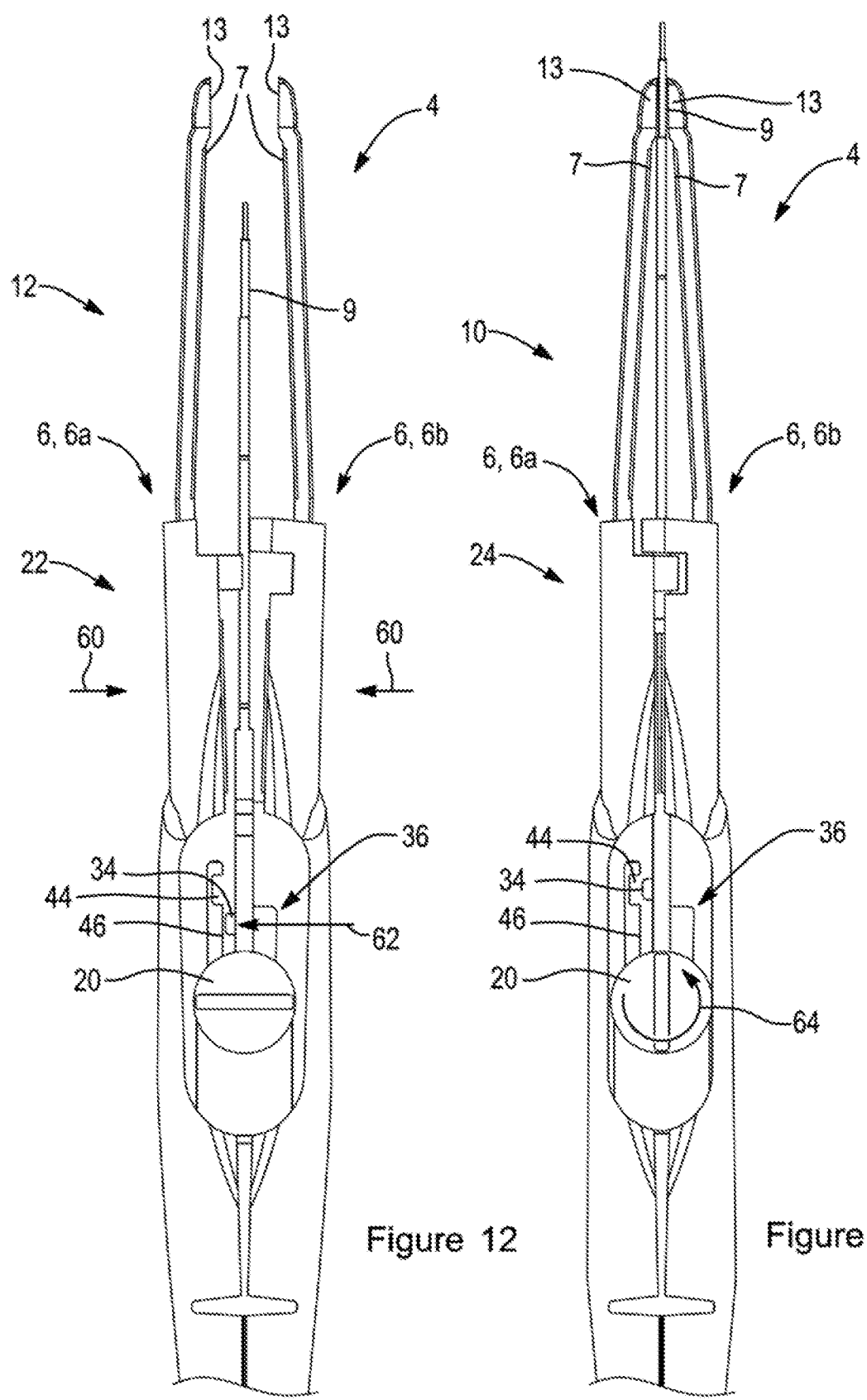

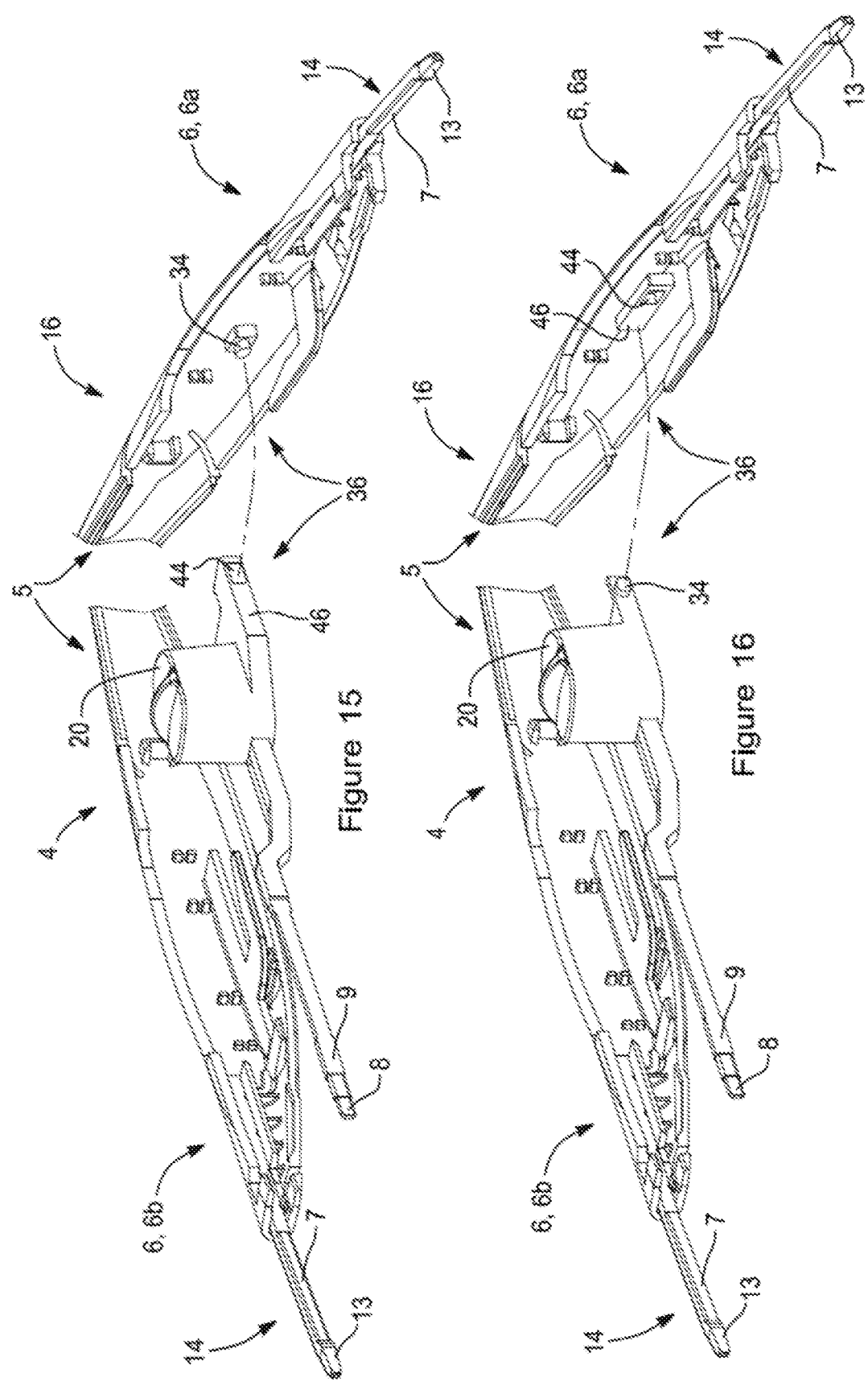

DISENGAGEMENT MECHANISM FOR ELECTROSURGICAL FORCEPS

FIELD

The present teachings generally relate to electrosurgical forceps that provide an electrical function automatically during gripping and more specifically a selectively engageable activation system that can be selectively switched on and off when the working arms are closed.

BACKGROUND

Current electrosurgical forceps when activated send a therapy current to the distal tips of the forceps via a push button on the hand piece or foot pedal. When the activation buttons are located on the hand piece, the buttons are activated by moving one or more fingers while trying to apply a clamping force, to a feature of interest such as a vessel, which can be difficult. Activation buttons on electrosurgical forceps type devices are also outside of the surgeons 'learned' hand skill, requiring the user to reprogram their intended hand coordination which in some individuals takes seconds, while in others it may be a number of procedures before this becomes an automatic response. Some surgeons find it difficult to locate and active buttons on the hand piece. Locating the buttons on the hand piece requires surgeons to change their hand movements and adjust coordination, which may affect the flow of a procedure or cause delay until the new hand movements become an automatic response. Conversely, using foot pedals may be challenging as surgeons may need to look away from the area of interest to identify the foot pedal for that specific device.

Devices that are automatically activated when the working arms are closed may be used, however, there is no way of turning off the function when the working arms are closed together and the function is no longer desired. This may result in a surgeon switching instruments in order to use nonelectrical forceps or use a button or foot pedal operated device, but would be subject to the limitations mentioned above.

Examples of some electrosurgical instruments may be found in U.S. Pat. Nos. 4,041,952 and U.S. Patent Publications 2014/0276795, all of which are incorporated by reference herein for all purposes. What is needed is an electrosurgical forceps that easily transforms between an electrical state which sends a therapy signal automatically when the working arms are closed together and a non-electrical state that does not send a therapy current when the working arms are closed together. It would be attractive to have a forceps with a squeeze-to-activate electrical function that is selectively engageable so the forceps can be switched between an electrosurgical forceps that deliver a therapy signal when the arms are brought together and standard, "cold" forceps, where no therapy signal passes through the device. It would be attractive to have an electrosurgical forceps with a squeeze-to-activate bipolar function in the first state, and a squeeze-to-activate monopolar function in the second state, where the electrosurgical forceps convert between the two states through the use of a shuttle.

SUMMARY

The present teachings meet one or more of the present needs by providing: an electrosurgical forceps comprising: (a) a pair of working arms comprising; (i) a first working arm and a second working arm, each of the first working arm and the second working arm having an inner surface; (ii) one or more electrodes located on the inner surface of the first working arm, the second working arm, or both; and (b) a selectively engageable activation system comprising; (i) a control unit; (ii) an activation switch; and (iii) a disengagement mechanism; wherein the first working arm and the second working arm are laterally movable relative to each other so that the activation switch is actuated when the disengagement mechanism is in an engaged position by closing the first working arm and the second working arm together, sending a signal to the control unit, which in turn sends a therapy signal to the one or more electrodes; wherein when the disengagement mechanism is in a disengagement position and the working arms are closed, the therapy signal is prevented from being sent from the control unit to the one or more electrodes.

The teachings herein provide an electrosurgical forceps that easily transforms between an electrical state which sends a therapy signal automatically when the working arms are closed together and a non-electrical state that does not send a therapy signal when the working arms are closed together. The teachings provide a forceps with a squeeze-to-activate electrical function that is selectively engageable so the forceps can be switched between an electrosurgical forceps that deliver a therapy signal when the arms are brought together and standard, "cold" forceps, where no therapy signal passes through the device. The teachings provide an electrosurgical forceps with a squeeze-to-activate bipolar function in the first state, and a squeeze-to-activate monopolar function in the second state, where the electrosurgical forceps convert between the two states through the use of a shuttle.

BRIEF DESCRIPTION OF THE DRAWINGS

FIG. 1 illustrates a perspective view of one example of the electrosurgical forceps in the disengagement position (Blade advanced).

FIG. 2 illustrates a perspective view of the electrosurgical forceps in the engagement position (Blade retracted).

FIG. 4 illustrates a top view of the socket and anvil surface disengagement mechanism in the engagement position.

FIG. 5 illustrates a top view of the socket and anvil surface disengagement mechanism in the disengagement position.

FIG. 6 illustrates a top view of the leaf spring mechanism disengagement mechanism in the engagement position.

FIG. 7 illustrates a top view of the leaf spring disengagement mechanism in the disengagement position.

FIG. 8 illustrates a top view of the activation switch guard disengagement mechanism in the engagement position.

FIG. 9 illustrates a top view of the activation switch guard disengagement mechanism in the disengagement position.

FIG. 10 illustrates a top view of the alternative socket and anvil surface disengagement mechanism in the engagement position.

FIG. 11 illustrates a top view of the alternative socket and anvil surface disengagement mechanism in the disengagement position.

FIG. 12 illustrates a top view of the electrosurgical forceps with a rotational shuttle in the engagement position.

FIG. 13 illustrates a top view of the electrosurgical forceps with a rotational shuttle in the disengagement position.

FIG. 15 illustrates a component view of the electrosurgical forceps with the anvil surface and socket on the working arm.

FIG. 16 illustrates a component view of the electrosurgical forceps with the activation switch on the working arm.

DETAILED DESCRIPTION

Figure 3:
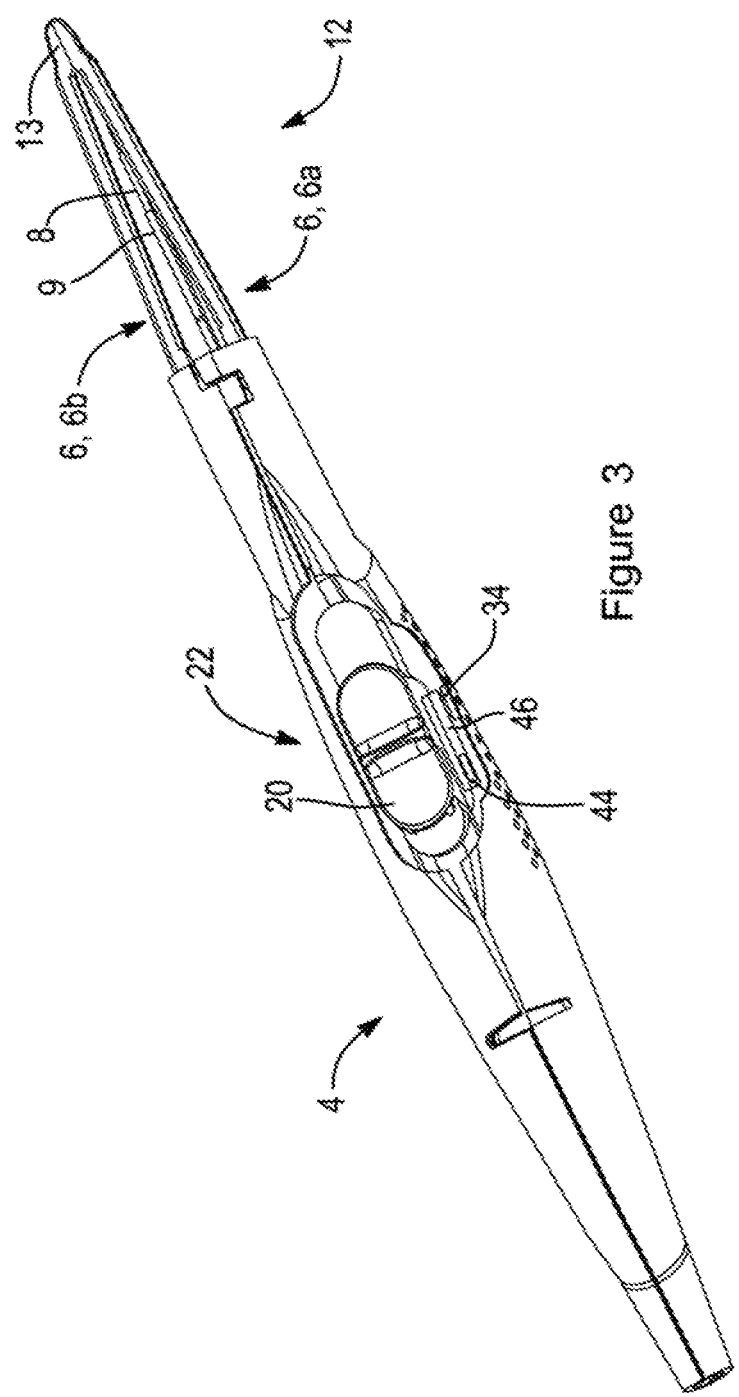
FIG. 3 illustrates a perspective view of the electrosurgical forceps in the engagement position with the arms closed.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a surgical device that is changeable between two functional states, with a first state providing a first function and a second state providing a second function. The surgical device may switch between a first electrical state and a second electrical state (which may be a non-electrical state). The surgical device in the first electrical state may function to generate a signal, provide power, or both. The surgical device in the second electrical state may function to grip, cut, clamp, pull, or a combination thereof. The surgical device may include one or more activation switches (e.g., 2 activation switches, 3 activation switches, 4 activation switches, 5 activation switches). The one or more activation switches may be used to actuate the one or more functional states of the surgical device when the working arms are closed together. The surgical device may be a mechanical surgical device, electromechanical surgical device (e.g., a device with a mechanically moving element and electrical element), an electrosurgical device, or a combination thereof. The surgical device may be part of a surgical system. Preferably, the present teachings relate to a surgical forceps and associated componentry that form an electronic, mechanical, or electromechanical surgical system, or a combination thereof.

The surgical system may include one or more of the devices taught herein. The surgical system may include one or more bodies as taught herein, one or more ground pads, one or more generators, one or more electrosurgical devices, one or more adjacent body components, or a combination thereof. Preferably, the surgical system includes a surgical device.

The surgical device may be used by a surgeon to perform a surgical procedure. The surgical device may function to be switched between two or more configurations, two or more states, or both. For example, the surgical device may be switched between an electrical state, a non-powered state, a different electrical state, or a combination thereof. The surgical device may be switched between two or more states with one hand so that the procedure is not disrupted. The surgical device may be used ambidextrously, ambidextrously switched between states, or both. The surgical device may be used for powered surgical purposes such as cutting, performing hemostasis, coagulating, desiccating, fulgrating, electrocautery, or a combination thereof. The surgical device may perform one or more functions. Preferably, the surgical device performs a plurality of functions. For example, the surgical device may perform a first function, second function, third function, fourth function, or more functions. The surgical device may include bipolar capabilities, monopolar capabilities, non-electrosurgical capabilities, or a combination thereof. The surgical device may be used in open surgery. The surgical device may be used for non-powered surgical purposes. For example, the surgical device may be used as forceps, tweezers, or both that may be used to grip an object, an organ, a vein, skin, tissue, or a combination thereof. Preferably, the surgical device is an electrosurgical forceps. In another example, one or more parts of the device may include a sharp edge and may be used to cut, similar to that of a scalpel. Preferably, the surgical device is a combination electrosurgical forceps with a retractable blade which switches between a first state and a second state.

The surgical device may have a first state and a second state. The first state may function to enable the surgical device to provide a first functional element. The second state may function to enable the surgical device to provide a second functional element. The state may be a relative disposition or arrangement of any part of the device that moves relative to another part. For example, the selectively engageable activation system moves the disengagement mechanism relative to the activation switch or vice versa so that the device changes between a first state (or first configuration) and a second state (or second configuration). The first state and the second state may be mechanical, electrical, electromechanical, or a combination thereof. The first state may be closed forceps, open forceps, a probe, a blade, provide a therapy signal, or a combination thereof. The second state may be closed forceps, open forceps, a probe, a blade, provide a therapy signal, or a combination thereof. For example, the first state is a forceps that provides a therapy signal when the first working arm and second working arm are closed together, actuating the activation switch, and the second state is the forceps in a non-electric state, where the device is free from sending a therapy signal when the first working arm and second working arm are closed together. In another example, the first state is a forceps and provides a bipolar therapy signal when the first working arm and second working arm are closed together and a second state is a probe that may be free of any therapy signal. In a further example, the first state is a forceps that provides a bipolar therapy sign when the working arms are closed together and the second state is a probe that provides a monopolar therapy signal when one or more exterior activation buttons are actuated. Changing the surgical device from the first state to the second state may change how the body of the surgical device interacts with other elements of the surgical device.

The surgical device has a body. The body may function to connect a functional element to a user interface. The body may provide power, signals, current, or a combination thereof to the functional element. The body and one or more functional elements may be one integral piece or the functional element may be removable from the body. The body may include a power source or be connected to a power source. The body of the device may house the components that are used to make the device functional. The body of the device can be a hand piece. The body of the device may be forceps. The body may be a frame. A frame may be a structure that underlies or supports the surgical device. The body of the device may connect working arms, one or more functional elements, or both. The body of the device has a distal end and a proximal end. The body of the device may include or be connected to one or more activation switches, a disengagement mechanism, a shuttle, a functional element, a selectively engageable activation system, a control unit, a pair working arms, or a combination thereof.

The selectively engageable activation system allows the user to change between a plurality of functions of the surgical device. The selectively engageable activation system functions to transform the device between an activatable state, a non-activatable state, a first activatable state, a second activatable state, or a combination thereof. The selectively engageable activation system may convert the device between an electrical state and a non-electrical state. The selectively engageable activation system may convert the device between a first electrical state and a second electrical state. The selectively engageable activation system may change the position of the disengagement mechanism relative to the body, the activation switch, the control unit, or a combination thereof. The selectively engageable activation system may be changeable between two or more positions so that two or more functions are enabled (e.g., 2 or more functions, 3 or more functions, 4 or more functions, 5 or more functions). The selectively engageable activation system may longitudinally move along the surgical device (e.g., may move in the direction of the longitudinal axis (e.g., a length) of the device (e.g., forceps)); rotationally move around a component of the surgical device (e.g., the selectively engageable activation system may follow the contour of the surgical device in a direction substantially perpendicular to the longitudinal axis); the selectively engageable activation system may laterally move (e.g., from side to side without following the contour of the device); or a combination thereof. The longitudinal axis as discussed herein is the dimension with the longest length. The selectively engageable activation system may move along or within one or more channels. The selectively engageable activation system may be moveable by a sliding action. The selectively engageable activation system may include a portion that is located on a surface of the surgical device and a portion that extends into the surgical device. The selectively engageable activation system may be on the body, removeably attached to a body, movable along the body, or a combination thereof. The selectively engageable activation system may consist of a control unit, an activation switch, a disengagement mechanism, a shuttle, or a combination thereof.

The disengagement mechanism allows the surgical device to engage the functional element or disengage the functional element. The disengagement mechanism may engage or disengage the functional element by facilitating or preventing the activation switch from being depressed. The disengagement mechanism may allow or prevent the activation switch actuation by moving relative to the body, the activation switch, the control unit, or a combination thereof. The disengagement mechanism may: longitudinally move along the surgical device (e.g., may move in the direction of the longitudinal axis of the device (e.g., forceps); rotationally move around a component of the surgical device (e.g., the disengagement mechanism may follow the contour of the surgical device in a direction substantially perpendicular to the longitudinal axis); laterally move on the device (e.g., from side to side without following the contour of the device); or a combination thereof. The disengagement mechanism may have at least two positions, an engagement position and a disengagement position. In the disengagement position the disengagement mechanism may be aligned with the activation switch, control unit, or both so that the functional element cannot be actuated. In the engagement position the disengagement mechanism may be misaligned with the activation switch, control unit, or both so that the functional element may be actuated. For example, when the disengagement mechanism is in the engagement position, the disengagement mechanism is misaligned with the activation switch so that when the working arms are closed together, the activation switch is actuated. In the disengagement position, the disengagement mechanism is aligned with the activation switch, so when the working arms are closed together, the activation switch is not actuated or is prevented from being actuated. The disengagement mechanism may consist of a shuttle, a socket, an anvil surface, a leaf spring mechanism, an activation switch guard, an activation switch, or a combination thereof.

The shuttle assists in converting the device between a plurality of states. The surgical device may be moved between a first state, second state, third state, fourth state, or more states by moving the shuttle. The shuttle may translate so that the shuttle: moves along a line or axis of the device; along a surface of the device; rotates as a knob on the device; or a combination thereof. For example, the shuttle may be rotated about a longitudinal axis of a working arm between an engagement position and a disengagement position. In another example, the shuttle may translate between an engagement position and a disengagement position by moving along the longitudinal axis of the working arms. The shuttle may move between positions (e.g., first, second, third, or fourth positions) as the shuttle moves along the device. The shuttle may longitudinally move along the surgical device (e.g., may move in the direction of the longitudinal axis of the device); rotationally move around a component of the surgical device (e.g., may follow the contour of the surgical device in a direction substantially perpendicular to the longitudinal axis); the shuttle may laterally move (e.g., from side to side without following the contour of the surgical device); or a combination thereof. The shuttle may move along the longitudinal axis of the surgical device. The shuttle may move in a direction substantially perpendicular to the longitudinal axis (i.e., laterally). The shuttle may move around a rotational axis that is substantially parallel to the longitudinal axis (i.e., rotationally). The shuttle may be in communication with the disengagement mechanism, the control unit, the activation switch, or a combination thereof. When the shuttle is in communication with the disengagement mechanism, the activation switch is stationary to the body. The shuttle may have two or more positions (e.g., at least a first position and a second position). The shuttle may have a plurality of positions. The shuttle may have a first position, second position, third position, fourth position, or more positions. The shuttle in one or more of the positions discussed herein may disable one or more of the states herein. The shuttle in a first position may disable a second electrical state, in a second position may disable a first electrical state and/or a third electrical state, or a combination thereof. For example, the shuttle converts the device between the first functional state and second functional state by moving the disengagement mechanism between the engagement position and the disengagement position. The shuttle may move between an engagement position and a disengagement position. The shuttle may include a socket, an anvil surface, a leaf spring mechanism, an activation switch guard, or a combination thereof, which enable or disable the user from actuating the activation switch.

The disengagement mechanism may include a socket. The socket functions to prevent actuation of the activation switch. The socket may cover the activation switch and prevent, obstruct, hinder, or a combination thereof actuation of the activation switch. The socket may allow or disallow the actuation of the activation switch depending on the position of the disengagement mechanism. The socket may be on the shuttle or the body. The socket may be located on one or both of the working arms (e.g., a surface of the working arms that faces a shuttle). The socket may be locate on a surface of the shuttle (e.g., a surface that faces a working arm or an activation switch). When the disengagement mechanism is in the disengagement position, the activation switch is aligned with the socket, allowing the activation switch to fit inside the socket. When the activation switch is located inside the socket, the activation switch is free from actuation when the first working arm and the second working arm are closed together. When the disengagement mechanism is in the engagement position, the socket and the activation switch are misaligned, so the activation switch is not located in the socket and is actuated when the first working arm and second working arm are closed. The socket may be a recess that receives the activation switch so that movement of the working arms towards each other does not actuate the activation switch. The socket may be a hole, a cavity, a depression, a chamber, a device that receives all or a portion of the activation switch, or a combination thereof. The socket may lock the activation switch so that the activation switch is prevented from being actuated. For example, the activation switch may have a piece that extends under the activation switch, between the activation switch and the working arms or shuttle, and prevents the activation switch from being depressed. The socket and activation button may be located on opposing surfaces so that the socket receives the activation switch when an therapy signal is not desired.

The disengagement mechanism may include an anvil surface. The anvil surface may function to actuate the activation switch. The anvil surface may actuate the activation switch when the device is in the engagement position by pressing against the activation switch when the first working arm and second working arm are closed together. The anvil surface may be located on the shuttle or the body. When the disengagement mechanism is in the engagement position, the activation switch may be aligned with the anvil surface, so that the activation switch is actuated by the anvil surface when the first working arm and second working arm are closed. When the disengagement mechanism is in the disengagement position the activation switch may be misaligned with the anvil surface, such that the activation switch is not actuated when the first working arm and second working arm are closed. The disengagement mechanism may include the socket for the activation switch and the anvil surface. For example, the disengagement mechanism is in the disengagement position and the activation switch is aligned with the socket. The activation switch is aligned with the socket, allowing the activation switch to fit into the socket so when the working arms are closed together, the activation switch is free from actuation by the anvil surface. The socket physically prevents the activation switch from being actuated by shielding the activation switch from making contact with the anvil surface. The disengagement mechanism in the engagement position places the activation switch out of alignment with the socket. When the activation switch is misaligned with the socket, the anvil surface can contact the activation switch. Upon closure of the workings arms together, the anvil surface presses against the activation switch, actuating the activation switch to enable the functional element.

The disengagement mechanism may include a leaf spring mechanism. The leaf spring mechanism may be in contact with the activation switch in the engagement position. The leaf spring mechanism may be connected to the first working arm, second working arm, shuttle, the first working arm, second working, or a combination thereof. The leaf spring mechanism may align with the activation switch in the engagement position and misalign with the activation switch in the disengagement position. For example, the leaf spring mechanism is connected to the first working arm, second working arm, or both, so when the shuttle is in the engagement position the leaf spring mechanism deflects when the working arms are closed together, which presses against the activation switch located on the shuttle, activating the functional element. When the shuttle is in the disengagement position, the leaf spring mechanism is free from actuating the activation switch when the first working arm and second working arm are closed because the leaf spring mechanism is misaligned with the activation switch located on the shuttle.

The disengagement mechanism may include an activation switch guard. The activation switch guard functions to prevent the activation switch from being actuated. The activation switch guard may be a piece of material that comes between the activation switch and the actuating surface of the device, physically preventing the activation switch from being depressed. The activation switch guard in the disengagement position may align with the activation switch and prevent the activation switch from being depressed when the first working arm and second working arm are closed. When the activation switch guard is in the engagement position, the activation switch guard may be misaligned with the activation switch, allowing the actuation of the activation switch when the first working arm and second working arm are closed. The activation switch guard may be located on the body, the shuttle, the first working arm, the second working arm, or a combination thereof. Preferably, the activation switch guard is located on the shuttle.

The activation switch may function to activate the functional elements of the device. The activation switch functions to receive one or more user inputs and control one or more functional elements of the surgical device. There may be more than one activation switch associated with the device (e.g., two activation switches, three activation switches, four activation switches, five activation switches). The activation switch may be located on the interior of the surgical device, the first working arm, the second working arm, the shuttle, or a combination thereof. The activation switch may be movable with the shuttle. The activation switch may be static (e.g., longitudinally or rotationally, but may be depressed by movement of the shuttle) relative to the shuttle. The activation switch may be located on an opposing piece of the forceps and may be actuated or protected when the shuttle moves between positions. For example, the activation switch may be located on the working arms and may be actuated by when the shuttle in in an engagement position and prevented from being actuated when the shuttle is in the disengagement position. The activation switch may be flat, convex, concave, a dome switch, a membrane switch, an electrical switch, a capacitive sensor, a pressure sensor, or a combination thereof. When the activation switch is actuated, the switch may complete a circuit, send a signal, or both. The activation switch, when actuated, may send a signal to the control unit.

The surgical device includes a pair of working arms. The working arms may be used to grab, pull, pinch, pry, probe, or a combination thereof. The working arms may include a first working arm and a second working arm. The working arms may include an inner surface. On the inner surface of the first working arm, second working arm, or both may reside one or more electrodes. The first working arm, second working arm, or both may be in communication with the disengagement mechanism, the activation switch, or both. When the device is in the disengagement position and the first working arm and second working arm are closed together, the activation switch may be depressed by the disengagement mechanism. When the activation switch is depressed by the selectively engageable activation system, a signal may be sent to the control unit. The control unit may send a therapy signal to the electrodes on the inner surface of the working arms.

The therapy signals may be a signal, power, continuity, or a combination thereof. The therapy signals may pass from the surgical device to the generator or vice versa. The therapy signals may be formed by the surgical device, formed by the generator, or both. The signals may be a therapy current. Preferably, the therapy signals indicate that a user has performed a step and a signal is being transmitted so that a therapy current, a therapy energy, or both is generated. The therapy signals may provide a signal so that one or more therapy currents are produced and the therapy currents may be used for electrosurgery. The therapy signal may be conducted when the surgical device is in a first state, a second state, a third state, the disengagement mechanism is in a first position, a second position, a third position, or a combination of surgical device states and disengagement mechanism positions. Preferably, a therapy signal is not generated, does not exit the surgical device, or both when the disengagement mechanism is in the disengagement position. The therapy signal may be a monopolar therapy signal, a bipolar therapy signal, or both. The therapy signal may be a monopolar therapy current, a bipolar therapy current, or both. The monopolar therapy signal may be any signal that has a voltage differential between a return port and an active port in the generator. The monopolar therapy signal may be any signal that when applied by the surgical device extends from one pole of the surgical device to another pole located at a remote location. The bipolar therapy signal may be any signal that has a voltage differential between two electrodes that are connected to the surgical device, that are located in the generator, or both. The bipolar therapy signal may be any signal that, when applied, extends from one component of the surgical device to another component of the surgical device (e.g., between two working arms, from a blade electrode to one or both working arms, or both). A therapy signal, when the disengagement mechanism is in the disengagement position, may exit the surgical device so that a therapy signal extends from a blade electrode, between the first working arm and the second working arm, between the blade electrode and one or both of the working arms, or a combination thereof. The therapy signal may be generated and conducted from the surgical device to the control unit.

The control unit may be any device that supplies power, therapy signals, control signals, electronically reconfigures itself in response to a signal from the user, physically reconfigures in response to adjustments by the user, or a combination thereof. The control unit may function to be electrically connected to the surgical device to provide and/or receive therapy signals, power, therapy current, or a combination thereof. The control unit may be capable of producing only a single therapy signal. The control unit may be capable of producing two therapy signals. The control unit may be capable of producing a plurality of therapy signals. The control unit may include two or more power connections, three or more power connections, or four or more power connections. The control unit may include one or more switches that may be switched between one or more of the power connections so that power, signals, or both may be selectively applied to the electrosurgical device based upon a desired configuration of the surgical device. The control unit may be a generator, a microprocessor, or both. Preferably, the control unit is a generator.

The generator may be any device that supplies power, therapy signals, therapy currents, control signals, electronically reconfigures itself in response to a signal from the user, physically reconfigures in response to adjustments by the user, or a combination thereof. The generator may function to be electrically connected to the surgical device to provide and/or receive therapy signals, power, therapy current, or a combination thereof. The generator may be capable of producing only a single therapy signal. The generator may be capable of producing two or more therapy signals. The generator may be capable of producing a plurality of therapy signals. The generator may include two or more power connections, three or more power connections, or four or more power connections. The power connections may be any port in the generator so that one or more power connectors of the surgical device may be plugged into so that power, therapy signals, control signals, therapy currents, or a combination thereof are supplied to the surgical device. The generator may include one or more switches that may be switched between one or more of the power connections so that power, signals, or both may be selectively applied to the surgical device based upon a desired configuration of the surgical device. The generator may include a central processing unit (CPU), a series of internal switching, or both. The internal switching may provide a signal from an activation circuit to the voltage source so that the voltage source is supplied to the surgical device. The CPU may be interchanged with the internal switching and the switching may perform the same functions as the CPU. The CPU may be any device that provides power, signals, electrical reconfiguration, a switch between two or more therapy currents, a switch between two or more configurations, a switch between two or more therapy signals, or a combination thereof to the electrosurgical device so that the electrosurgical device may be used to perform a desired function as is discussed herein. The CPU may be used to switch the surgical device between a first configuration, a second configuration, a third configuration, a monopolar configuration, a bipolar configuration, a non-electrosurgical configuration, or a combination thereof by sending or not sending one or more therapy signals.

The surgical device may also include one or more exterior activation buttons that, when actuated, enable one or more therapy signals. Exterior activation buttons are used to actuate one or more functional elements when the device is in the second state. The exterior activation buttons may be covered and/or unexposed in the first state. The exterior activation buttons may be uncovered and/or exposed in the second state. The exterior activation buttons may be located on the exterior of the surgical device. The exterior activation buttons may be covered and uncovered by the shuttle, the disengagement mechanism, or both. For example, the surgical device is in the first state and the shuttle is in the engagement position. When the shuttle is in the engagement position, the exterior activation buttons are covered. When the shuttle is moved from the engagement position to the disengagement position, the surgical device is converted into the second state and the exterior activation buttons are uncovered. The exterior activation buttons may actuate in the second state the same functional element as the first state. The exterior activation buttons may actuate a different functional element than the first state.

The one or more functional elements are an integral part of the surgical device or a part that may be added to the surgical device so that the surgical device may be used to perform a surgical procedure. The surgical device has at least one functional element. Preferably, the surgical device has more than one functional element. The functional elements may be electrical elements. Electrical elements use electricity to perform one or more portions of a surgical procedure. The electrical functional element may be an electrode, an electrical motor, an ultrasonic transducer, or a combination thereof. The surgical device may have at least one electrical element. The surgical device may have at least two electrical elements. The surgical device may have a plurality of electrical elements. The functional element of the surgical device may be a mechanical function. A mechanical function is substantially free of electricity or any other power source. The mechanical function may be using the surgical device to cut, grip, probe, saw, or a combination thereof. For example, a mechanical device is a forceps. For example, a mechanical device is a scalpel. The surgical device may be a combination of electrical and nonelectrical functional elements. For example, the surgical device may be electrosurgical forceps where in the first state the electrosurgical forceps produce a therapy current and in the second state the surgical device would function as non-electrical forceps.

The surgical device may be a combination device. A combination device incorporates two or more structural elements into a single device to make a tool that is capable of performing multiple functions without switching handsets. For example, the surgical device in the first state is an electrosurgical forceps and in the second state is a bladed cutting tool.

FIG. 1 illustrates a perspective view of one example of a surgical device 1 that is shown as an electrosurgical device 2. The electrosurgical device 2 is an electrosurgical forceps 4 that includes a body 5. The electrosurgical forceps 4 has a distal end 14 and a proximal end 16. The distal end 14 includes a pair of working arms 6, having a first working arm 6a, a second working arm 6b, and a blade 9 with a blade electrode 8 therebetween. The working arms 6a, 6b, respectively, have an inner surface 7 and an electrode 13. The blade 9 is advanced forward into the first state 10 by the shuttle 20 being moved forward into a disengagement position 24 (i.e. along the longitudinal axis 18). The activation switch 34 is carried on the first working arm 6a. An anvil surface 46 and socket 44 are carried on the shuttle 20. In the disengagement position 24, the activation switch 34 is aligned with the socket 44, and the activation switch 34 is misaligned with the anvil surface 46 so that the activation switch is free from actuation by the anvil surface 46. The first exterior activation button 26 and the second exterior activation button 28 are exposed when the shuttle 20 is in the disengagement position 24.

FIG. 2 illustrates a perspective view of the electrosurgical forceps 4 in the second state 12 with the shuttle 20 in the engagement position 22. In the second state, the blade 9 with the blade electrode 8 is retracted between the pair of working arms 6. When the shuttle 20 is in the engagement position 22, the activation switch 34 (located on the shuttle 20) is misaligned with the socket 44 (located on the first working arm 6a) so when the first working arm 6a and the second working arm 6b are closed together in a lateral movement 60, the anvil surface 46 actuates the activation switch 34, sending a therapy signal through the electrodes 13 on the interior surface 7. The first exterior activation button and second exterior activation button are covered when the electrosurgical forceps are in the engagement position 22.

FIG. 3 illustrates a perspective view of the electrosurgical forceps 4 in the second state 12 when the working arms 6 are actuated to a closed position by a user. In the second state 12, the shuttle 20 is in the engagement position 22 and the pair of working arms 6, are closed together. When the first working arm 6a and the second working arm 6b are closed together, the anvil surface 46 actuates the activation switch 34 and the socket 44 is misaligned with the activation switch 34. Upon actuation of the activation button 34, a therapy signal is sent to the electrodes 13 located on the interior surface 7 of the working arms 6. In the second state 12 the blade 9 with the blade electrode 8 is retracted.

FIG. 4 illustrates a top view of the socket 44 and anvil disengagement mechanism 36 in the engagement position 22. The shuttle 20 carries the anvil surface 46 and the socket 44. The activation switch 34 (on the first working arm 6a) is aligned with the anvil surface 46, so when the first working arm 6a and the second working arm 6b are closed together with a lateral movement 60, the anvil surface 46 actuates the activation switch 34 in the activation direction 62. The blade 9 in the engagement position 22 does not extend past the pair of working arms 6.

FIG. 5 illustrates a top view of the socket 44 and anvil disengagement mechanism 36 in the disengagement position 24. When the shuttle 20 is moved from the engagement position 24 to the disengagement position 24, in translational direction 66, the socket 44 aligns with the activation switch 34 so that the activation switch 34 extends into the socket 44 when the first working arm 6a and the second working arm 6b are moved together. In the engagement position 24, the activation switch 34 is free from actuation by the anvil surface 46 when the first working arm 6a and the second working arm 6b are brought together, and the exterior activation buttons 26, 28 are exposed. The blade 9 advances between the pair of working arms 6 in direction 66.

FIG. 6 illustrates a top view of the disengagement mechanism 36, which is a leaf spring 48, in the engagement position 22. The leaf spring 48 is deflected against the anvil surface 46 when the first working arm 6a and the second working arm 6b are closed with a lateral movement 60. When the pair of working arms 6 are moved by a lateral movement 60 and brought together, the leaf spring 48 actuates the activation switch 34 in the activation direction 62. In the engagement position 22, blade 9 is not extended past the working arms 6.

FIG. 7 illustrates a top view of the disengagement mechanism 36, which is a leaf spring 48, in the disengagement position 24. When the shuttle is moved to the disengagement position 24, in translational direction 66, the anvil surface 46 is moved so that the leaf spring 48 and anvil surface 46 are misaligned and the leaf spring 48 and activation switch 34 are free from deflection off of the anvil surface 46. In the disengagement position 24 the shuttle 20 is located in a distal position with the blade 9 extending between and partially distal of the first working arm 6a and the second working arm 6b, and the working arms are moved together about the blade 9. As shown, exterior activation buttons 26, 28 are exposed by the shuttle 20 being located in the distal position.

FIG. 8 illustrates a top view of the disengagement mechanism 36, which is an activation switch guard 50, in the engagement position 22. The shuttle 20 aligns the anvil surface 46 with the activation switch 34, so when the first working arm 6a and the second working arm 6b are closed together with a lateral movement 60, the anvil surface 46 actuates the activation switch 34 in the activation direction 62. When the shuttle 20 is in the engagement position 22 the activation switch guard 50 is misaligned with the activation switch 34 and the blade 9 does not extend past the pair of working arms 6.

FIG. 9 illustrates a top view of the disengagement mechanism 36, which is an activation switch guard 50, in the disengagement position 24. The shuttle 20 advances in the translational direction 66, advancing the activation switch guard 50. The activation switch guard 50 is brought into alignment with the activation switch 34 so that the anvil surface 46 cannot actuate the activation switch 34. The first working arm 6a and the second working arm 6b are brought together and the blade 9 is advanced through the working arms 6. The exterior activation buttons 26, 28 are exposed when the shuttle 20 is advanced in the translational direction 66.

FIG. 10 illustrates a top view of a disengagement mechanism 36 with a socket 44 and anvil surface 46 in the engagement position 22. The shuttle 20 carries the activation switch 34 and aligns the activation switch 34 with the anvil surface 46 on the first working arm 6a. When the first working arm 6a and the second working arm 6b are brought together with the lateral movement 60, the activation switch 34 actuates against the anvil surface 46 in the activation direction 62. As shown, the activation switch 34 is misaligned with the socket 44, and blade 9 does not extend past the pair of working arms 6.

FIG. 11 illustrates a top view of a disengagement mechanism 36 including a socket 44 and anvil surface 46 in the disengagement position 24. The shuttle 20 advances in the translational direction 66, which brings the first working arm 6a and the second working arm 6b together. The activation switch 34 is now aligned with the socket 44, so the activation switch 34 is free from actuation by the anvil surface 46. As shown, the exterior activation buttons 26, 28 are exposed and the blade 9 is advanced past the pair of working arms 6.

FIG. 12 illustrates a top view of the electrosurgical forceps 4 in the second state 12. The first working arm 6a and the second working arm 6b have an interior surface 7 with electrodes 13 located on the ends. In the second state 12, the disengagement mechanism 36 is in the engagement position 22. The shuttle 20 aligns the activation switch 34 with the anvil surface 46 and misaligns the activation switch 34 with the socket 44 and retracts the blade 9. When the pair working arms 6 is brought together with a lateral movement 60, the activation switch 34 is actuated by the anvil surface 46 in the activation direction 62.

FIG. 13 illustrates a top view of the electrosurgical forceps 4 in the first state 10. In the first state 10, the disengagement mechanism 36 is in the disengagement position 24. The shuttle 20 rotates 64 and extends the blade 9 so that the activation switch 34 is aligned with the socket 44 and the activation switch is not depressed by contacting the anvil surface 46. Rotating the shuttle 20 to the first state 10 advances the blade 9 and brings the first working arm 6a and the second working arm 6b together. The electrodes 13 on the interior surface 7 are absent of a therapy signal.

Figure 14:
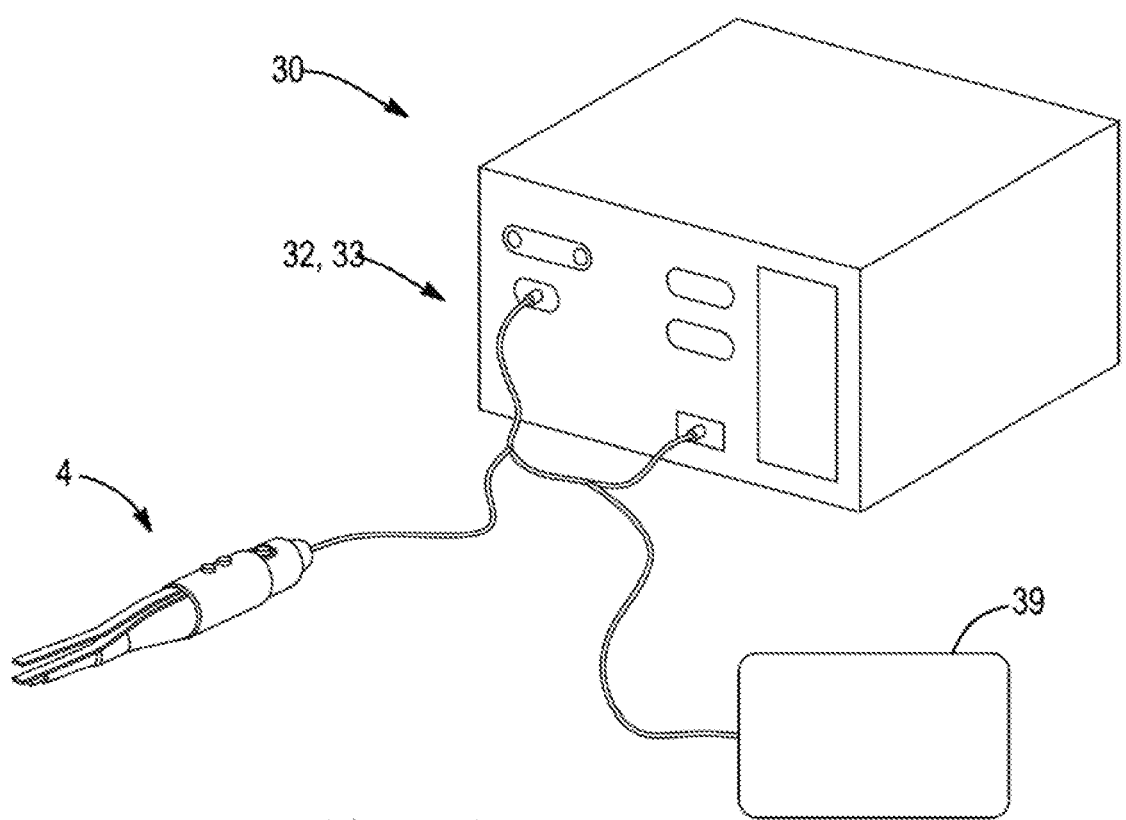
FIG. 14 illustrates a perspective view of the electrosurgical forceps and control unit.

FIG. 14 illustrates a perspective view of the electrosurgical forceps 4 with the selectively engageable activation system 30. The selectively engageable activation system 30 includes a control unit 32, which is illustrated as an electrosurgical generator 33. The electrosurgical forceps 4 and a ground pad 39 are connected to the control unit 32.

FIG. 15 illustrates an partial exploded view of the electrosurgical forceps 4. The body 5 holds the pair of working arms 6. The first working arm 6a and the second working arm 6b have an interior surface 7. At the distal end 14, the first working arm 6a and the second working arm 6b have an interior surface 7. The interior surface includes an electrode 13. The activation switch 34 is located on an interior surface 7 of the first working arm 6a. The shuttle 20 holds the blade 9 which includes a blade electrode 8. The disengagement mechanism 36 is shown to include the shuttle 20, activation switch 34, the anvil surface 46, and the socket 44. The shuttle 20 carries the anvil surface 46 and the socket 44.

FIG. 16 illustrates a partial exploded view of the electrosurgical device 4. The body 5 holds the pair working arms 6. The first working arm 6a and the second working arm 6b have an interior surface 7. The distal end 14 of the working arms 6 include an interior surface 7. Located on the interior surface 7 is an electrode 13. The interior surface 7 of the first working arm 6a holds the anvil surface 46 and the socket 44. The shuttle 20 holds the blade 9 which includes a blade electrode 8. The disengagement mechanism 36 is shown to include the shuttle 20, activation switch 34, the anvil surface 46, and the socket 44.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. An electrosurgical forceps comprising:
   a. a pair of working arms comprising;
      i. a first working arm and a second working arm, each of the first working arm and the second working arm having an inner surface;
      ii. one or more electrodes located on the inner surface of the first working arm, the second working arm, or both; and
   b. a selectively engageable activation system comprising;
      i. a control unit;
      ii. an activation switch; and
      iii. a disengagement mechanism located between the first and second working arms and positioned proximal to the one or more electrodes, the disengagement mechanism movable between an engagement position and a disengagement position;
   wherein the first working arm and the second working arm are laterally movable relative to each other between an open position and a closed position when the disengagement mechanism is in both the engagement position and the disengagement position;
   wherein when the disengagement mechanism is in the engagement position and the first and second working arms are moved from the open position to the closed position, the activation switch is depressed by the disengagement mechanism and sends a signal to the control unit, which in turn sends a therapy signal to the one or more electrodes; and
   wherein when the disengagement mechanism is in the disengagement position and the first and second working arms are moved from the open position to the closed position, the activation switch is not depressed by the disengagement mechanism and the therapy signal is prevented from being sent from the control unit to the one or more electrodes.

2. The electrosurgical forceps of claim 1, wherein the disengagement mechanism includes a shuttle which moves between the engagement position and the disengagement position.

3. The electrosurgical forceps of claim 2, wherein the disengagement mechanism includes a socket that receives the activation switch when the shuttle is in the disengagement position so that the activation switch is not actuated when the first working arm and second working arm are moved to the closed position, and the socket, in the engagement position, is misaligned with the activation switch so that the activation switch is actuated when the first working arm and the second working arm are moved to the closed position.

4. The electrosurgical forceps of claim 2, wherein the disengagement mechanism includes an anvil surface that is aligned with the activation switch in the engagement position so that the activation switch is actuated by the anvil surface when the first working arm and the second working arm are moved to the closed position, and the anvil surface, in the disengagement position, is misaligned with the activation switch so the activation switch is not actuated when the first working arm and the second working arm are moved to the closed position.

5. The electrosurgical forceps of claim 2, wherein the disengagement mechanism includes a socket and an anvil surface, so when the shuttle is in the disengagement position the activation switch is aligned with the socket, allowing the activation switch to fit into the socket such that the switch is free from actuation when the first working arm and the second working arm are moved to the closed position, and when the shuttle is in the engagement position, the activation switch is aligned with the anvil surface, so that the activation switch is actuated by the anvil surface when the first working arm and second working arm are moved to the closed position.

6. The electrosurgical forceps of claim 2, wherein the disengagement mechanism includes a leaf spring in contact with the activation switch, so when the shuttle is in the engagement position the leaf spring deflects, actuating the activation switch when the first working arm and second working arm are moved to the closed position, and when the shuttle is in the disengagement position, the leaf spring is free from actuating the activation switch, when the first working arm and second working arm are moved to the closed position.

7. The electro surgical forceps of claim 2, wherein the disengagement mechanism includes an activation switch guard such that:
   when the shuttle is in the disengagement position, the activation switch guard aligns with the activation switch and obstructs the activation switch from being depressed when the first working arm and second working arm are moved to the closed position; and
   when the shuttle is in the engagement position, the activation switch guard is misaligned with the activation switch, allowing the activation switch to be actuated when the first working arm and second working arm are moved to the closed position.

8. The electrosurgical forceps of claim 4, wherein the activation switch is carried on the shuttle.

9. The electrosurgical forceps of claim 2, wherein the shuttle rotates between the engagement position and the disengagement position.

10. The electrosurgical forceps of claim 2, wherein the shuttle translates between the engagement position and the disengagement position.

11. The electrosurgical forceps of claim 2, wherein the shuttle in the disengagement position exposes one or more exterior activation buttons and the shuttle in the engagement position covers the exterior activation buttons.

12. The electrosurgical forceps of claim 11, wherein the exterior activation buttons, when depressed, send one or more therapy currents through the first working arm, second working arm, or both.

13. The electrosurgical forceps of claim 1, further comprising a blade.

14. The electrosurgical forceps of claim 13, wherein the blade is connected to a shuttle, and the blade in the engagement position is not exposed, and in the disengagement position the blade is extended beyond the first working arm and second working arm.

15. The electrosurgical forceps of claim 10, wherein the blade has an electrode.

16. The electrosurgical forceps of claim 14, wherein the shuttle in the disengagement position exposes one or more exterior activation buttons, that, when depressed, send one or more therapy currents through the first working arm, the second working arm, the blade, or combination thereof and the shuttle in the engagement position covers the one or more exterior activation buttons.

17. The electrosurgical forceps of claim 16, wherein when the one or more exterior activation buttons are depressed, one or more therapy currents are sent between the blade and an electrode that is remote from the blade.

18. An electrosurgical forceps comprising:
 a. a pair of working arms comprising;
  i. a first working arm and a second working arm, each of the first working arm and the second working arm having an inner surface;
  ii. one or more electrodes located on the inner surface of the first working arm, the second working arm, or both; and
 b. a selectively engageable activation system comprising;
  i. a control unit;
  ii. an activation switch carried on the first working arm; and
  iii. a disengagement mechanism located between the first and second working arms and positioned proximal to the one or more electrodes, the disengagement mechanism movable between an engagement position and a disengagement position;
 wherein the first working arm and the second working arm are laterally movable relative to each other between an open position and a closed position when the disengagement mechanism is in both the engagement position and the disengagement position;
 wherein when the disengagement mechanism is in the engagement position and the first and second working arms are moved from the open position to the closed position, the activation switch is depressed by the disengagement mechanism and sends a signal to the control unit, which in turn sends a therapy signal to the one or more electrodes; and
 wherein when the disengagement mechanism is in the disengagement position and the first and second working arms are moved from the open position to the closed position, the activation switch is not depressed by the disengagement mechanism and the therapy signal is prevented from being sent from the control unit to the one or more electrodes.

19. An electrosurgical forceps comprising:
 a. a pair of working arms comprising;
  i. a first working arm and a second working arm, each of the first working arm and the second working arm having an inner surface;
  ii. one or more electrodes located on the inner surface of the first working arm, the second working arm, or both; and
 b. a selectively engageable activation system comprising;
  i. a control unit;
  ii. an activation switch; and
  iii. a disengagement mechanism located between the first and second working arms and positioned proximal to the one or more electrodes, the disengagement mechanism including at least one of a socket, an anvil surface, or a leaf spring, the disengagement mechanism movable between an engagement position and a disengagement position, thereby moving the at least one of a socket, an anvil surface, or a leaf spring relative to the activation switch;
 wherein the first working arm and the second working arm are laterally movable relative to each other between an open position and a closed position when the disengagement mechanism is in both the engagement position and the disengagement position;
 wherein when the disengagement mechanism is in the engagement position and the first and second working arms are moved from the open position to the closed position, the activation switch is depressed by the disengagement mechanism and sends a signal to the control unit, which in turn sends a therapy signal to the one or more electrodes; and
 wherein when the disengagement mechanism is in the disengagement position and the first and second working arms are moved from the open position to the closed position, the activation switch is not depressed by the disengagement mechanism and the therapy signal is prevented from being sent from the control unit to the one or more electrodes.

* * * * *